United States Patent [19]
Ando et al.

[11] 4,105,520
[45] Aug. 8, 1978

[54] METHOD FOR PRODUCING ADIPIC ACID AND PRECURSORS THEREOF

[75] Inventors: Wataru Ando, Sakura; Ichiro Nakaoka, Machida, both of Japan

[73] Assignee: Kabushiki Kaisha Pollution Preventing Research Laboratory, Tokyo, Japan

[21] Appl. No.: 785,666

[22] Filed: Apr. 7, 1977

Related U.S. Application Data

[63] Continuation-in-part of Ser. No. 717,179, Aug. 24, 1976, abandoned.

[30] Foreign Application Priority Data

Feb. 26, 1977 [JP] Japan ................................. 52-19819
Apr. 9, 1976 [JP] Japan ................................. 51-39270

[51] Int. Cl.² .............................................. B01J 1/10
[52] U.S. Cl. ......................... 204/162 R; 204/162 XN
[58] Field of Search .................................. 204/162 R

[56] References Cited

FOREIGN PATENT DOCUMENTS 1,026,034 4/1966 United Kingdom ................ 204/162 R
1,070,750 6/1967 United Kingdom ................ 204/162 R

*Primary Examiner*—Leland A. Sebastian
*Attorney, Agent, or Firm*—Fitzpatrick, Cella, Harper & Scinto

[57] ABSTRACT

A method for producing adipic acid and precursor thereof which comprises oxidizing cyclohexane with nitrogen dioxide under irradiation of visible ray or ultraviolet ray in the presence of oxygen is incorporated with a method for producing adipic acid which comprises oxidizing said precursor with liquid nitrogen dioxide $N_2O_4$ at a temperature below the boiling point thereof. It should be noted that the precursor means cyclohexanone, cyclohexanol, cyclohexylnitrite, cyclohexylnitrate or the mixture thereof.

8 Claims, 2 Drawing Figures

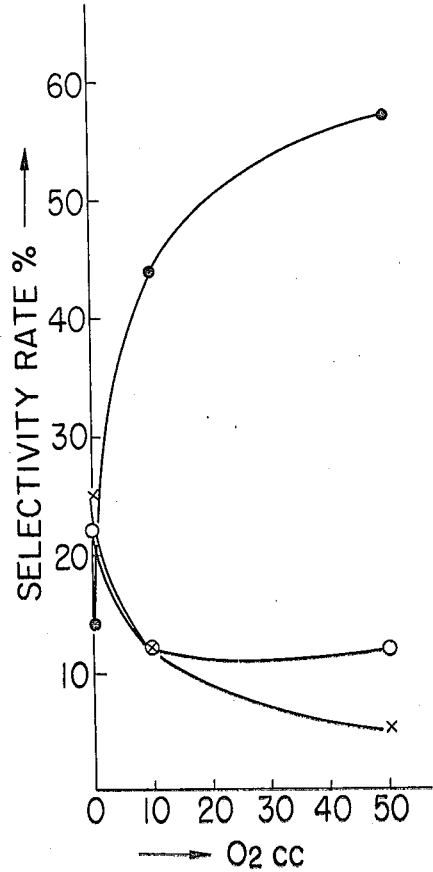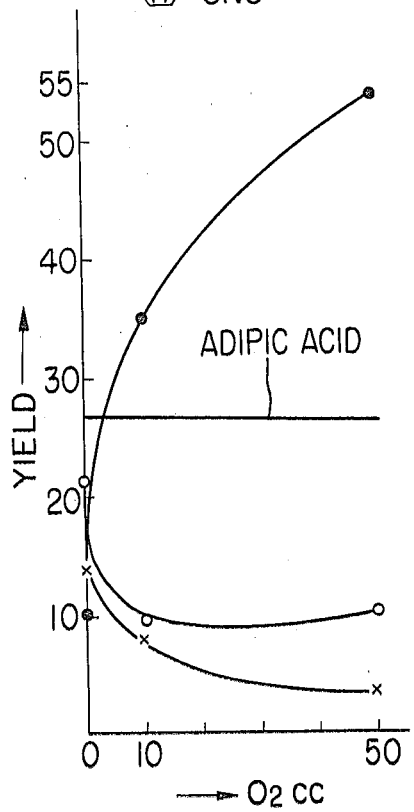

METHOD FOR PRODUCING ADIPIC ACID AND PRECURSORS THEREOF

This application is a continuation-in-part of application Ser. No. 717,179, filed Aug. 24, 1976, now abandoned, now Ser. No. 868,294, filed Jan. 10, 1978 and Ser. No. 782,165, filed Mar. 28, 1977.

BACKGROUND OF THE INVENTION a. Field of the Invention

This invention relates to a method for oxidizing cyclohexane with nitrogendioxide, and followed by oxidizing the intermediate product i.e. said precursor with liquid nitrogendioxide $N_2O_4$ for the purpose of producing adipic acid.

b. Description of the Prior Art

A number of prior arts of producing adipic acid have been known. In the industrial scale, adipic acid has been produced by a method by which acrylnitrile is dimerized by electrochemical hydrogenation to form dinitrile, and followed by hydrolysis of it, and also by the alternative method by which hydrogenation is effected to dimerize acrylnitrile in dimethyl sulfoxide by the use of sodium amalgam.

In the large scale production, however, adipic acid has been principally produced by oxidizing cyclohexane.

Hereinafter, mainly, the methods of producing adipic acid directly from cyclohexane are mentioned. 1. Chemical Technology 1974(9) disclosed on page 555 – 559 that adipic acid was produced by oxidizing cyclohexane by molecular oxygen under a pressure, at a temperature about 80° – 90° C in the presence of catalyst and initiator in acetic acid. The selectivity rate of adipic acid was 72 – 74%, and conversion rate of cyclohexane was 82 – 88%. 2. Ullmann Encyclopaedia Der Technische Chemie Bd. 3 (1953) disclosed on page 95 that cyclohexane was oxidized by nitric acid under a pressure of 2 – 15 atm at a temperature of 90° – 120° C in about 12 hours to produce adipic acid in an yield about 34% with nitrocyclohexane in an yield about 16%.

Furthermore, the following methods are known. 3. Japanese Patent Publication No. 3812/1964 disclosed that cyclohexane reacted with nitrogendioxide at a temperature of 30° – 70° C in the presence of catalyst in 120 hours to produce adipic acid in an yield about 30% with nitrocyclohexane in an yield about 5%. 4. Roberto Lee, et al disclosed on page 411 – 420 Industrial and Engineering Chemistry Process Design and Development Vol 4, No. 4 1965 that cyclohexane reacted with nitrogendioxide in vapor phase to investigate variables including temperature, residence time, molar ratio of cyclohexane to nitrogendioxide and several different reactors. Nitrocyclohexane was obtained in an yield about 50% with other product such as adipic acid, cyclohexylnitrite, cyclohexylnitrate, cyclohexanone and cyclohexanol. 5. William F. Hoot et al disclosed on page 783 Industrial and Engineering Chemistry Vol. 47, No. 4 1955 nitrogendioxide was dissolved in cyclohexane and the mixture was allowed to react at a temperature of 50° – 90° C. Adipic acid was obtained at 50° C in an yield of 98% in 43 hours, but in an yield of 5% in 2 hours. 6. A. Toptschien et al disclosed on page 1367 – 1368 B. 67 (1934) that cyclohexane reacted with nitrogendioxide under irradiation of ultraviolet ray in the presence of carbondioxide at temperature of 30° and 80° C in about one hour to produce nitrocyclohexane in an yield about 30% and 25% with no formation of adipic acid. 7. Japanese Patent Publication No. 24094/1969 disclosed that cyclohexane reacted with nitrogendioxide under irradiation of ultraviolet ray at a temperature of 25° C in about 3 hours to produce adipic acid in a selectivity rate about 86% with nitrocyclohexane in selectivity rate about 8%. The conversion rate, however, of cyclohexane was about 10% so that the yield of adipic acid was low. 8. Japanese Patent Application No. 148908/1974 disclosed that cyclohexane reacted with nitrogendioxide under irradiation of ultraviolet ray or visible ray at a room temperature in the presence of oxygen to produce cyclohexanone, cyclohexanol and cyclohexylnitrite. However, adipic acid was not formed. 9. A. I. Titov et al disclosed on pages 241 and 242 J. Gem. Chem. USSR 23 (1953) that 350 ml cyclohexane reacted with 20g nitrogendioxide dissolved in 50 ml hydrocarbon at a temperature of 60° C in 16 hours by introducing 3 l oxygen and 5.1g adipic acid and 6.7g nitrocyclohexane were obtained, and that 0.5g cyclohexane reacted with 1.4g nitrogendioxide at a temperature of 100° C in 3 hours to obtain 0.21g adipic acid with 0.04g nitrocyclohexane. 10. A. I. Titov disclosed on page 567 Tetrahedron 1963 Vol. 19 the free radical mechanism of nitration. However, there was no disclosure of photochemical oxidation of cyclohexane with nitrogendioxide in the presence of oxygen. 11. In Chemischen Information Dienst 22 Juli 1975, there is a description "Beim Einleiten von Ozonisierten Sauerstoff und Stickoxid bzw Stickstoffdioxid in Cyclohexan." In this report, the formation of adipic acid was found, but this reaction was not photochemical reaction.

SUMMARY OF THE INVENTION

The present invention relates to a method of producing adipic acid and precursor thereof whereby cyclohexane reacts with nitrogen dioxide under irradiation of visible ray or ultraviolet ray in the presence of oxygen and, followed successively by the reaction of said precursor with liquid nitrogendioxide $N_2O_4$ at a temperature below the boiling point thereof to produce adipic acid.

The invention relates to the improvement of the inventions described in U.S. patent application Ser. Nos. 868,294, filed Jan. 10, 1978, a continuation of U.S. Ser. No. 717,179, filed Aug. 26, 1976, now abandoned, and 782,165, filed Mar. 28, 1977. That is to say, the composition of the present invention is explained as follows. The first step is to prepare reaction product containing adipic acid and precursor thereof based on the photochemical reaction disclosed herein and in Japanese Patent Application No. 39, 270/1976, for which priority is claimed. The second step is to separate said adipic acid from said precursors, and the third step is to oxidize the precursor with liquid nitrogendioxide $N_2O_4$ to produce adipic acid based on the ionic reaction disclosed in the U.S. patent application Ser. No. 868,294, cited hereinabove.

The present invention, in particular, relates to a method for producing adipic acid which comprises a series of steps of reacting cyclohexane with nitrogen dioxide under irradiation of visible ray or ultraviolet ray in the presence of oxygen to prepare adipic acid and precursor thereof, removing unreacted nitrogen dioxide, if necessary, adding a solvent to extract said precursor, taking out remaining crude adipic acid by means of insoluble liquid, washing said adipic acid with said solvent, incorporating said extract solution of precursor with said washing solution of adipic acid, removing said solvent from said incorporated solution to obtain the precursor or to concentrate said incorporated solution to a desired volume, and followed by adding precursor or said concentrated precursor solution to liquid nitrogendioxide $N_2O_4$ by which the precursor is oxidized to produce adipic acid.

The photochemical reaction was carried out at a temperature below 30° C and the ionic reaction was performed at a temperature below the boiling point of liquid nitrogendioxide $N_2O_4$. It is preferable that the precursor or the solution of it in a solvent is added to liquid nitrogen dioxide $N_2O_4$ of greater quantity than the theoretical quantity for the purpose of removing the exothermic reaction heat. The alternative method may be carried out at which liquid nitrogendioxide $N_2O_4$ in solvent or $N_2O_4$ being added to the precursor in a solvent solution.

In the above reactions, excess or unreacted oxide of nitrogen may be recovered as nitrogendioxide or liquid nitrogendioxide by oxidation and cooling.

After the photochemical reaction, formed nitrocyclohexane, cyclohexanol, cyclohexanone, cyclohexylnitrate and nitrite, and cyclohexane may be separated from adipic acid by means of a solvent and, if desired, the solvent solution containing those compounds may be treated by fractional distillation to obtain each product, individually. Cyclohexane may be recycled and the other product may be oxidized by the conventional method to produce adipic acid or may be used as a useful material.

The method of the present invention may be regarded to be advantageous to produce cyclohexylnitrate known as a useful diesel fuel additive.

In the Japanese Patent Application No. 39270/1976, we disclosed the simultaneous production method of adipic acid and precursor thereof, and suggested that the overall yield of adipic acid might be increased by considering the summation of said adipic acid and an additional adipic acid which might be obtained from said precursor.

In the U.S. application Ser. No. 868,294, cited hereinbefore, each precursor was oxidized with liquid nitrogendioxide $N_2O_4$ to produce adipic acid, individually.

On the other hand, in the method of the present invention, adipic acid formed in the photochemical reaction was separated from the simultaneously formed precursor which was followed successively by the reaction with liquid nitrogendioxide $N_2O_4$ without pre-separation by fractional distillation. The reaction may be assumed to proceed in such a manner that cyclohexylnitrate and nitrite in the mixture of precursor were principally oxidized to produce adipic acid almost in a theoretical yield, while cyclohexanol and cyclohexanone was oxidized, in part, to adipic acid, and some cyclohexanol and cyclohexanone and all nitrocyclohexane remained.

Therefore, the method of the present invention is different from the conventional method and novel as the direct method for producing adipic acid from cyclohexane.

The object of the present invention is to provide a direct method of producing adipic acid from cyclohexane which is comparable to or surpassing those of the conventional method in connection with reaction conditions such as temperature, pressure, time, and catalyst.

The object of the present invention is to use nitrogen dioxide as the initiator and reactant of the photochemical reaction. (the first step of the present invention) and, furthermore, to use liquid nitrogen dioxide $N_2O_4$ as the reactant of the ionic reaction. (the third step of the present invention) In other words, $NO_x$ in the effluent gas from the combustion of petroleum, natural gas and so on is oxidized to nitrogendioxide by the conventional method, if necessary liquefied it to liquid state $N_2O_4$ by cooling.

Also, there is an alternative source of nitrogen dioxide which is NO gas formed in a nitric acid production apparatus operating under the ammonia contact oxidation method. NO gas is oxidized, cooled and liquefied as liquid nitrogendioxide $N_2O_4$ and it may be vaporized to use as nitrogendioxide $NO_2$.

The foregoing objects, other objects and the reactions to take place in the method of the present invention will become more apparent and understandable from the following detailed explanation of the invention, when read in connection with several preferred examples thereof.

BRIEF DESCRIPTION OF THE DRAWING

FIGS. 1 and 2 indicate diagrammatically the data of table 1.

In FIG. 1, ordinate indicates the selectivity rate of each product based on cyclohexane and abscissa indicates the oxygen volume used.

In FIG. 2, ordinate indicates the yield of adipic acid and precursor thereof and abscissa indicates the oxygen volume used.

DESCRIPTION OF THE PREFERRED EMBODIMENT

The hypothetical mechanism of the photochemical reaction of the present invention will be shown wherein the situation of cyclohexane is in liquid phase and/or vapor phase and the situation of nitrogendioxide is as radical $NO_2\cdot$ or $NO\cdot$ in vapor phase or/and liquid phase, and the reaction is regarded as chain mechanism.

(1)

(2)

(3)

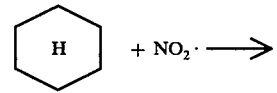

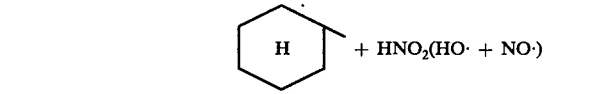

(4)

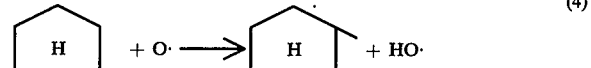

(5)

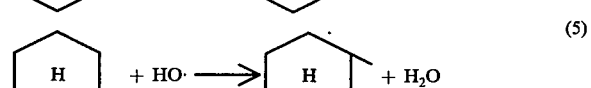

(6)

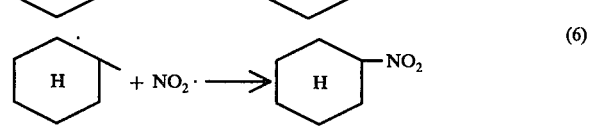

-continued
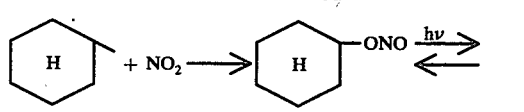 (7)
 (8)
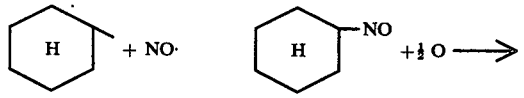 (9)
 (10)
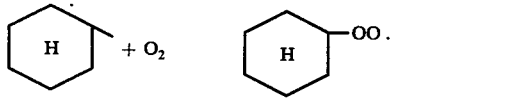 (11)
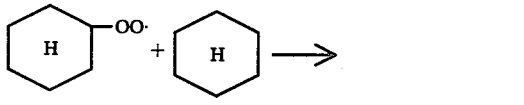 (12)
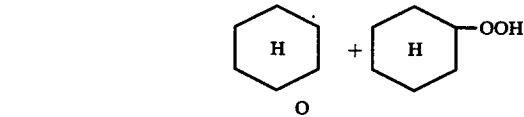 (13)
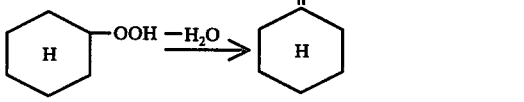 (14)
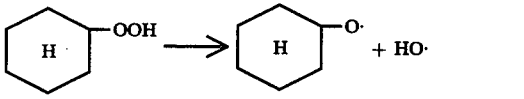 (15)
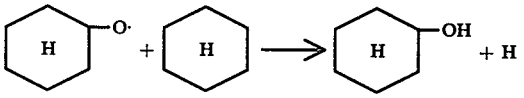 (16)
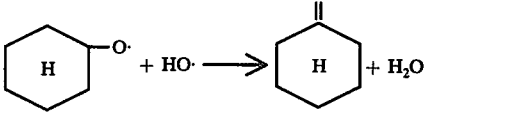 (17)
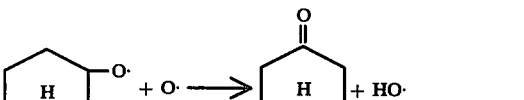 (18)
-continued
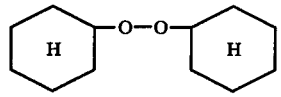 (19)
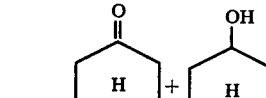 (20)
 (21)
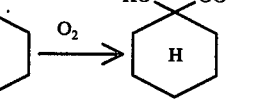 (22)
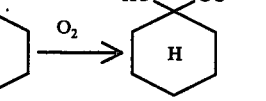 (23)
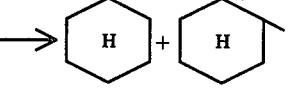 (24)
 (25)
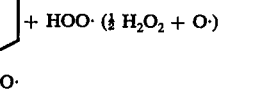 (26)
 (27)
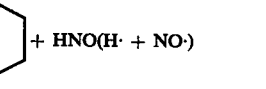 (28)
 (29)

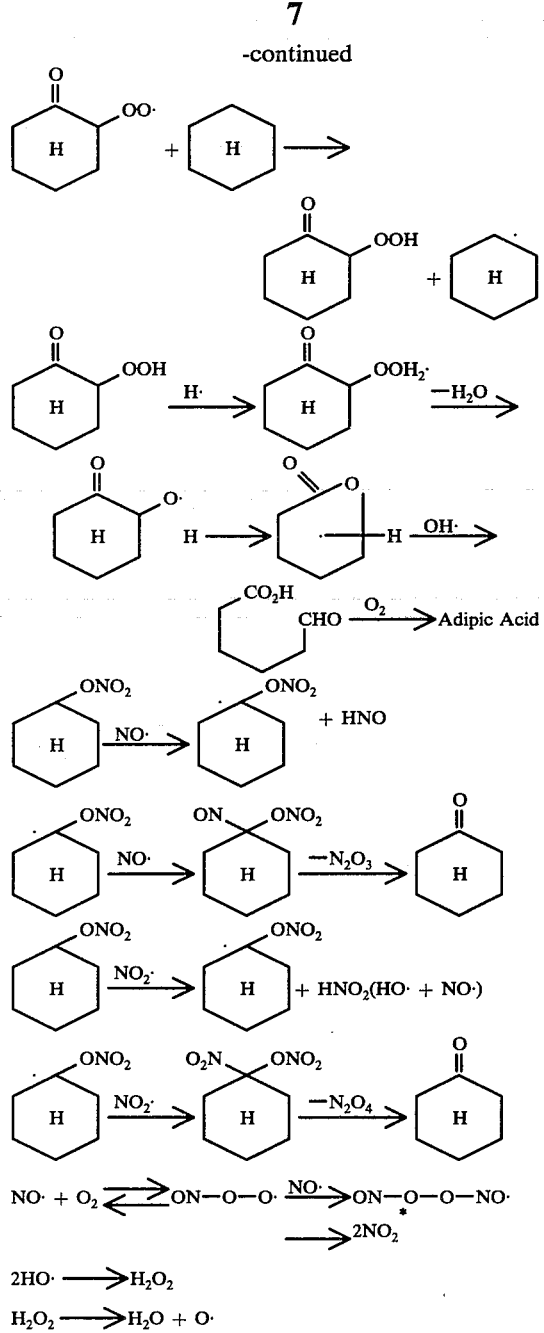

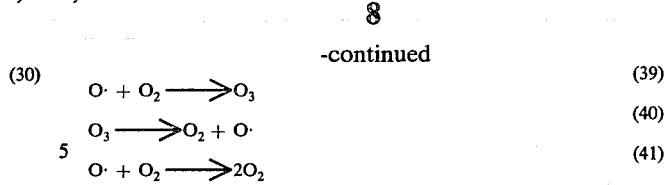

$$O\cdot + O_2 \longrightarrow O_3 \quad (39)$$

$$O_3 \longrightarrow O_2 + O\cdot \quad (40)$$

$$O\cdot + O_2 \longrightarrow 2O_2 \quad (41)$$

As is evident, the co-existence of both oxygen and nitrogendioxide is the absolute and indispensable requisite in the photochemical reaction of the present invention.

The hypothetical mechanism of the reaction of liquid nitrogendioxide $N_2O_4$ with the precursor such as cyclohexanone, cyclohexanol, cyclohexylnitrate and nitrite might be regarded as ionic reaction disclosed on the United States Application Serial No. 868,294, formerly (U.S. patent application Ser. No. 717,179, now abandoned).

In summary of the foregoing, the characteristic feature of the present invention consists in the incorporation of the method for producing adipic acid and precursor thereof from cyclohexane by the photochemical reaction with the method for producing adipic acid by the ionic reaction at which liquid nitrogendioxide $N_2O_4$ reacts with said precursor at a temperature below the boiling point of liquid nitrogendioxide $N_2O_4$.

In order to enable those persons skilled in this art to readily perform the present invention into practice, the following preferred examples are presented.

It should, however, be noted that those examples are merely illustrative and not restrictive, and that any change and modification may be made by those skilled in the art in respect of the various reaction conditions as mentioned in the foregoing without departing from the spirit and scope of the present invention as set forth in the appended claims.

Experiment - 1 a. Method:

400 ml pyrex glass tube was degassed in which cyclohexane, nitrogendioxide and oxygen were introduced and closed. The reaction mixture was irradiated by means of high pressure mercury lamp at a temperature of 10° C in 2 – 3.5 hours. After removing oxide of nitrogen, the resulted products were extracted with ether, followed by directly quantitative analysis by means of gas chromatography. The identification of products was performed by Infrared Spectrum and nuclear magnetic resonance. (NMR).

b. Results of experiment

The results were indicated on the Table - 1.

Table 1

| | Quantity of reactant | | | Reaction | | Reaction product % | | | | | | Recovered |
|---|---|---|---|---|---|---|---|---|---|---|---|---|
| | | | | | | C₆H₁₁-NO₂ | | C₆H₁₁-OH | C₆H₁₀=O | C₆H₁₁-ONO | C₆H₁₁-ONO₂ | C₆H₁₂ |
| No | C₆H₁₂ μ | NO₂ cc | O₂ cc | Temperature °C | Time h | | (CH₂)₄(COOH)₂ | | | | | |
| 1 | 100 | 20 | 20 | 10 | 2.5 | 30 | 34 | | 8 | | 23 | 5 |
| 2 | 100 | 20 | — | 10 | 2.5 | 32 | 44 | | 10 | | 9 | 5 |
| 3 | 100 | 10 | — | 10 | 2.0 | 13 | 24 | | 15 | | 8 | 40 |
| 4 | 100 | 50 | 50 | 10 | 3.5 | 15 | 24 | | 2 | | 29 | 30 |
| 5 | 100 | 10 | 50 | 10 | 3.0 | 11 | 26 | | 4 | | 54 | 5 |
| 6 | 100 | 10 | 10 | 10 | 2.0 | 9 | 28 | | 9 | | 35 | 19 |

Table 1-continued

| No | Quantity of reactant C₆H₆ μ | NO₂ cc | O₂ cc | Reaction Temperature °C | Time h | C₆H₅NO₂ % | (CH₂)₄(COOH)₂ % | C₆H₅OH % | C₆H₅=O % | C₆H₅ONO % | C₆H₅ONO₂ % | Recovered C₆H₆ |
|---|---|---|---|---|---|---|---|---|---|---|---|---|
| 7 | 100 | 5 | 25 | 10 | 2.0 | 1 | 34 | | 4 | | 11 | 50 |

Note:

C₆H₆ 100 μ = 0.93 m mol
NO₂ 10cc = 0.45 m mol
O₂ 10 cc = 0.45 m mol

As shown in Table - 1 and FIGS. 1 and 2, in the method of the present invention, the yield of adipic acid is in the range of 24 – 34%. Therefore, these yield is about 3 – 4 times that of the Japanese Patent Publication No. 24094/1969, which no formation of adipic acid was recognized at the photochemical reaction of the other references. Furthermore, it should be noted that the yield of cyclohexylnitrate increased remarkably depend on the ratio of oxygen to nitrogendioxide, in particular, as the molar ratio of cyclohexane to oxygen was stoichiometric.

Experiment - 2

1. Method a. First step 300 ml pyrex glass tube was degassed in which 100 μ cyclohexane, 10 cc or 20 cc nitrogendioxide and 50 cc oxygen were introduced and closed. The reaction mixture was irradiated at a temperature of 25° – 30° C in 2.5 – 3 hours, by means of high pressure mercury lamp.

b. Second step

After removing oxide of nitrogen, the resulting products were extracted with 20 cc dichloromethane, but the crude solid remained in the tube which being taken out by means of insoluble liquid, for example, methanol, and washed with dichloromethane. This washed solution was incorporated with the extracted dichloromethane solution. Thus, this incorporated solution was concentrated to a volume about 3 cc under a reduced pressure.

c. Third step

Said concentrated dichloromethane solution was added to 0.5 cc liquid nitrogendioxide N₂O₄, while the temperature of the reaction mixture was maintained between 18° – 20° C during the reaction. After removing liquid N₂O₄, the remained solid was washed with 20 cc dichloromethane which was incorporated with the solid obtained at the second step. Thus, the total solid was purified. The identification of adipic acid was made by its Infrared Spectrum. Ethylendichloride, ethylendi-bromide, chloroform, bromoform and carbontetrachloride may be used as solvent.

The products in the photochemical reaction were extracted with dichloromethane and directly analyzed by gas chromatography. This results and the quantity of obtained adipic acid are indicated in Tables 2 and 3.

Table 2

Analytical Data of products from photochemical reaction by chromatography

| No | Quantity of reactant C₆H₆ μ | NO₂ cc | O₂ cc | Reaction Temperature °C | Time h | C₆H₅NO₂ % | C₆H₅OH % | C₆H₅=O % | C₆H₅ONO % | C₆H₅ONO₂ % | (CH₂)₄(COOH)₂ | Unreacted C₆H₆ % |
|---|---|---|---|---|---|---|---|---|---|---|---|---|
| 1 | 100 | 10 | 50 | 25 | 3 | 10 | 13 | | 45 | 15 | | 17 |
| 2 | 100 | 10 | 50 | 29 | 3 | 15 | 10 | | 41 | 15 | | 19 |
| 3 | 100 | 20 | — | 25 | 2.5 | 30 | 10 | | 15 | 20 | | 25 |

Note:

C₆H₆ 100 μ = 0.93 m mol, NO₂ 10 cc = 0.45 m mol O₂ 10 cc = 0.45 mmol

Table 3

| | Quantity of obtained adipic acid mg | | |
|---|---|---|---|
| No. | First step (photochemical reaction) | Third step (ionic reaction) | Total |
| 1 | 20 | 65 | 85 |
| 2 | 20 | 62 | 82 |
| 3 | 27 | 28 | 55 |

Note: Each adipic acid 85, 82, and 55 mg corresponds to the yield of 63, 61 and 41 % based on cyclohexane, respectively.

As shown in Tables 2 and 3, adipic acid was obtained in an overall yield of 63%, 61% and 41% based on cyclohexane. It should be noted that the minimum yield 41% was closely correlated with the minimum yield 15% of cyclohexylnitrate obtained in the photochemical reaction in the absence of oxygen. It should be understood that oxygen was the absolute and indispensable element as well as nitrogendioxide in the photochemical reaction of the method of the present invention.

The overall yield of adipic acid was approximately the same in comparison with the yield obtained by the direct method of producing adipic acid from cyclohexane in the prior art.

In addition, it should be considered that the conditions of the photochemical reaction might be modified in order to increase the yield of adipic acid and cyclohexylnitrate and, also that the conditions of the ionic reaction might be varied to increase the yield of adipic acid from cyclohexanone and cyclohexanol.

In brief, in the method of the present invention the reaction proceeds easily at a low temperature and pressure in the absence of catalyst to obtain adipic acid having high purity so that the purification of it is very simple.

We claim:

1. the method for producing adipic acid and precursors thereof which comprises reacting cyclohexane with nitrogen dioxide under irradiation of visible rays or ultraviolet rays in the presence of oxygen characterized in that cyclohexane reacts with the stoichiometric quantity or a quantity less than stoichiometry of nitrogendioxide and a quantity less than stoichiometry of oxygen.

2. The method as defined in claim 1 characterized in that molar ratio of cyclohexane to nitrogendioxide is 1 : 1 or 1 : above 1.

3. The method as defined in claim 1 characterized in that molar ratio of oxygen to nitrogendioxide is 1 : 1 or 1 : above 1.

4. The method for producing adipic acid and precursors thereof which comprises reacting cyclohexane with nitrogendioxide under irradiation of visible rays or ultraviolet rays in the presence of oxygen characterized in that cyclohexane reacts with the stoichiometric quantity or a quantity less than stoichiometry of nitrogendioxide and the stoichiometric quantity or a quantity more than stoichiometry of oxygen.

5. The method as defined in claim 4 characterized in that cyclohexane reacts with the stoichiometric quantity or a quantity less than stoichiometry of nitrogendioxide and molar ratio of oxygen to nitrogendioxide is 1 : above 1.

6. The method for producing adipic acid from cyclohexane which comprises the series of steps of (i) reacting cyclohexane with nitrogen dioxide under irradiation of visible rays or ultraviolet rays in the presence of oxygen to form adipic acid and precursors thereof, (ii) removing remaining oxides of nitrogen, (iii) adding a solvent to extract said precursors and separate them from said adipic acid, (iv) concentrating said extracted solution of the precursors and thereafter (v) adding said concentrated precursor solution to liquid nitrogen dioxide $N_2O_4$ to produce adipic acid from said precursors by oxidation and ring cleavage.

7. The method as defined in claim 6 characterized in that liquid nitrogendioxide $N_2O_4$ reacts with said precursors at a temperature below the boiling point of liquid $N_2O_4$.

8. The method as defined in claim 7 characterized in that cyclohexane reacts with the stoichiometric quantity or a quantity less than stoichiometry of nitrogendioxide and the quantity of stoichiometry or a quantity more than stoichiometry of oxygen.

* * * * *